United States Patent [19]

Kurahashi et al.

[11] Patent Number: 5,849,767
[45] Date of Patent: *Dec. 15, 1998

[54] CHLOROPYRIDYLCARBONYL DERIVATIVES

[75] Inventors: Yoshio Kurahashi, Tochigi; Haruko Sawada, Ibaraki; Haruhiko Sakuma, Tochigi; Taro Kinbara, Tochigi; Koichi Moriya, Tochigi; Koichi Ishikawa, Tochigi; Asami Motonaga, Tochigi, all of Japan

[73] Assignee: Nihon Bayer Agrochem K.K., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 708,995

[22] Filed: Sep. 6, 1996

[30] Foreign Application Priority Data

Sep. 13, 1995 [JP] Japan .................................. 7-259525
Jun. 21, 1996 [JP] Japan .................................. 8-179857

[51] Int. Cl.$^6$ .......................... A01N 43/50; C07D 401/06
[52] U.S. Cl. ........................................ 514/341; 546/274.7
[58] Field of Search ........................ 546/274.7; 514/341

[56] References Cited

U.S. PATENT DOCUMENTS 3,772,315  11/1973  Regel et al. .
4,474,599  10/1984  Rogers et al. .
4,966,908  10/1990  Eckhardt et al. ....................... 514/340
5,112,840   5/1992  Zondler et al. .......................... 514/341

FOREIGN PATENT DOCUMENTS 588357    3/1994  European Pat. Off. .
1926206  11/1970  Germany .
54-84032   4/1979  Japan .
55-113706  9/1980  Japan .
9418179    8/1994  WIPO .
9427983   12/1994  WIPO .

OTHER PUBLICATIONS

Patent Abstract of Japan, vol. 4, No. 173, Abstract No. JP 55–113706, (1980).
Patent Abstracts of Japan, vol. 3, No. 114, Abstract No. of JP 54–084,032, (1979).
S. Ohta, Heterocycles, vol. 23, No. 7, pp. 1759–1764, (1985).
Chemical Abstracts, vol. 124, No. 17, Abstract No. 232468r, p. 1456, Abstract of EP 690,061, (1996).
Chemical Abstracts, vol. 120, Abstract No. 292136h, p. 338, Abstract of JP 06 65,237, (1994).
Chemical Abstracts, vol. 102, p. 581, Abstract No. 185, 077w, (1985).
Chemical Abstracts, vol. 74, p. 307, Abstract No. 31754f, Abstract of DE 1,926,206, (1971).
Chemical Abstracts, vol. 66, p. 252, vol. 2431z, (1967).

Primary Examiner—Patricia L. Morris
Attorney, Agent, or Firm—Sprung Kramer Schaefer & Briscoe

[57] ABSTRACT

Novel chloropyridylcarbonyl derivatives of the formula

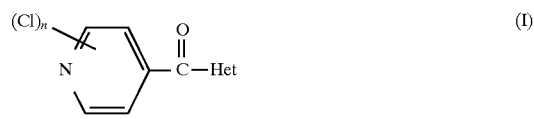

in which
Het is

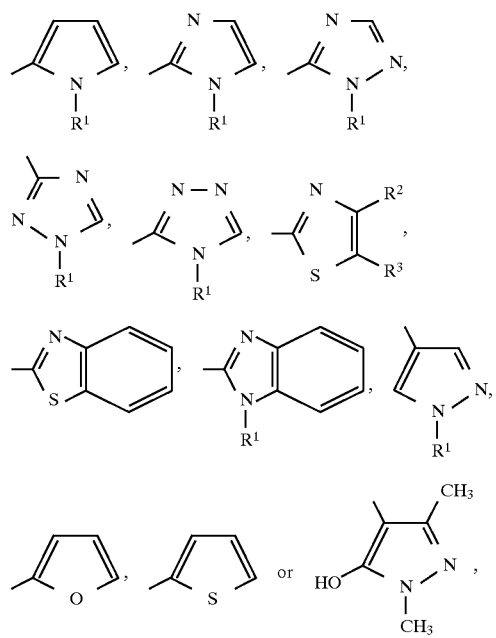

n is 1 or 2,
R$^1$ is hydrogen, optionally substituted C$_{1-6}$ alkyl, optionally substituted C$_{2-6}$ alkenyl, optionally substituted C$_{3-6}$ alkynyl, optionally substituted phenyl or optionally substituted pyrimidinyl, and
R$^2$ and R$^3$, independently of each other, are hydrogen or C$_{1-4}$ alkyl,
and acid addition salts and metal salt complexes thereof, are outstandingly active as microbicides.

5 Claims, No Drawings

CHLOROPYRIDYLCARBONYL DERIVATIVES

The present invention relates to novel chloropyridylcarbonyl derivatives, to processes for their preparation and to their use as microbicides.

It is already known that various pyrazole and acylimidazole derivatives have pharmaceutical properties or can be used for the preparation of compounds having pharmaceutical or fungicidal activities (see JP-As (Japanese published patent application) Sho 60-13764, Hei 6-65237 and Hei 8-53464, JP-B (Japanese published patent application after examination) Sho 51-7669, DE-A 1 926 206, Heterocycles 23 1957–1964 (1985), Chim. Therap. 1966, 127–136 and Chem. Abstr. 66, 2431z).

There have now been found novel chloropyridylcarbonyl derivatives of the formula $$(Cl)_n\text{-pyridyl-C(=O)-Het} \quad (I)$$

in which

Het is

[structures shown with substituents $R^1$, $R^2$, $R^3$]

n is 1 or 2, $R^1$ is hydrogen, optionally substituted $C_{1-6}$ alkyl, optionally substituted $C_{2-6}$ alkenyl, optionally substituted $C_{3-6}$ alkynyl, optionally substituted phenyl or optionally substituted pyrimidinyl, and $R^2$ and $R^3$, independently of each other, are hydrogen or $C_{1-4}$ alkyl, and acid addition salts and metal salt complexes thereof.

It has furthermore been found that chloropyridylcarbonyl derivatives of the formula (I) and acid addition salts and metal salt complexes thereof can be prepared by a) reacting chloropyridylcarbonyl halides of the formula $$(Cl)_n\text{-pyridyl-C(=O)-Hal} \quad (II)$$

in which n has the above-mentioned meaning and

Hal represents halogen, with heterocycles of the formula $$\text{Het}^1\text{—H} \quad (III)$$

in which $\text{Het}^1$ is

[structures shown with substituents $R^2$, $R^3$, $R^4$]

wherein $R^2$ and $R^3$ have the above-mentioned meanings and $R^4$ is optionally substituted $C_{1-6}$ alkyl optionally substituted $C_{2-6}$ alkenyl, optionally substituted $C_{3-6}$ alkynyl, optionally substituted phenyl or optionally substituted pyrimidinyl, in the presence of an inert diluent and, if appropriate, in the presence of an acid-binder and, if appropriate, in the presence of a catalyst, or b) reacting chloropyridylcarbonyl derivatives of the formula $$(Cl)_n\text{-pyridyl-C(=O)-Het}^2 \quad (Ia)$$

in which n has the above-mentioned meaning and

Het² represents

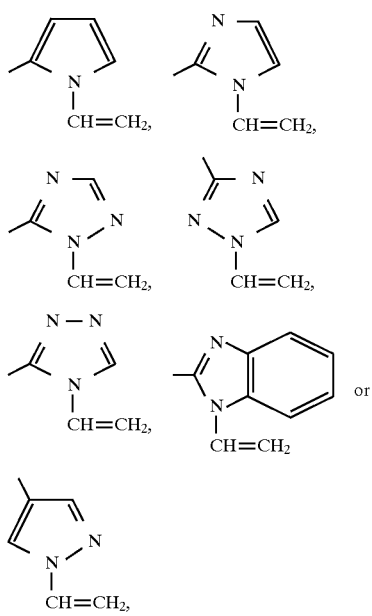

with periodic acid or their salts in the presence of osmium (IV)oxide and in the presence of an inert diluent, or c) reacting chloropyridylcarbonyl derivatives of the formula

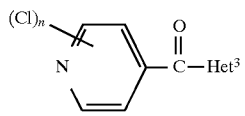 (Ib)

in which
  n has the above mentioned meaning and
  Het³ represents

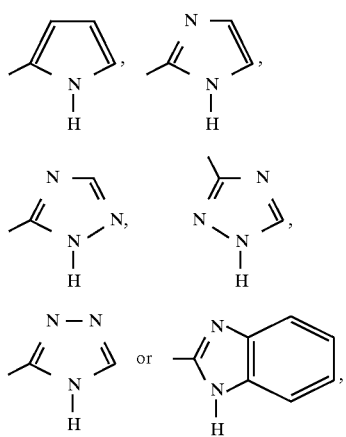

with halogeno compounds of the formula

   (IV)

in which
  R⁴ has the above-mentioned meaning and
  Hal¹ is halogen,
  in the presence of an inert diluent and, if appropriate, in the presence of an acid-binder and, if appropriate, in the presence of a catalyst, and, if appropriate, adding an acid or a metal salt onto the compounds of the formula (I) thus obtained.

Finally, it has been found that the chloropyridylcarbonyl derivatives of the formula (I) and acid addition salts and metal salt complexes thereof are outstandingly active as microbicides, which can be used in agriculture and horticulture. They can either be used for directly combating undesired microorganisms, such as phytopathogenic fungi and bacteriae or for inducing in the plant bodies themselves resistance to phytopathogenic fungi and bacteriae.

Surprisingly, the compounds according to the invention have a much better fungicidal activity than the already known compounds which are structurally most similar and have the same type of action.

In the present case, "alkyl", "alkenyl" and "alkynyl" represent straight-chain or branched groups. The term "$C_{1-6}$ alkyl" includes, for example, methyl, ethyl, n- or iso-propyl, n-, iso- or tert-butyl, n-pentyl and n-hexyl. The term $C_{2-6}$ alkenyl includes, for example, vinyl, allyl, 2- or 3-butenyl, 2-, 3- or 4-pentenyl, 3-methyl-2-butenyl, 2-, 3-, 4- or 5-hexenyl. The term $C_{3-6}$ alkynyl includes, for example, propargyl, 2- or 3-butynyl, 2-, 3- or 4-pentynyl, 2-, 3-, 4- or 5-hexynyl.

These alkyl, alkenyl and alkynyl groups may be substituted.

The possible substituents include, for example, halogen (e.g. fluorine, chlorine, bromine, iodine), phenyl, cyano, $C_{1-6}$ alkoxy (e.g. methoxy, ethoxy), $C_{1-6}$ alkylthio (e.g. methylthio, ethylthio), $C_{1-6}$ alkyl-carbonyl (e.g. methylcarbonyl, ethylcarbonyl, propylcarbonyl, tert-butylcarbonyl), $C_{1-6}$ alkoxy-carbonyl (e.g. methoxycarbonyl, ethoxycarbonyl), $C_{1-6}$ alkylaminocarbonyl (e.g. methylaminocarbonyl, ethylaminocarbonyl), di($C_{1-6}$ alkyl)aminocarbonyl (e.g. dimethylaminocarbonyl, diethylaminocarbonyl, methylethylaminocarbonyl), hydroxyimino, $C_{1-6}$ alkoxyimino (e.g. methoxyimino, ethoxyimino) and the like. If the alkyl, alkenyl and alkynyl groups are substituted by two or more substituents, then the substituents may be identical or different.

Formula (I) provides a general definition of the chloropyridylcarbonyl derivatives according to the invention. Preferred compounds of the formula (I) are those, in which Het is

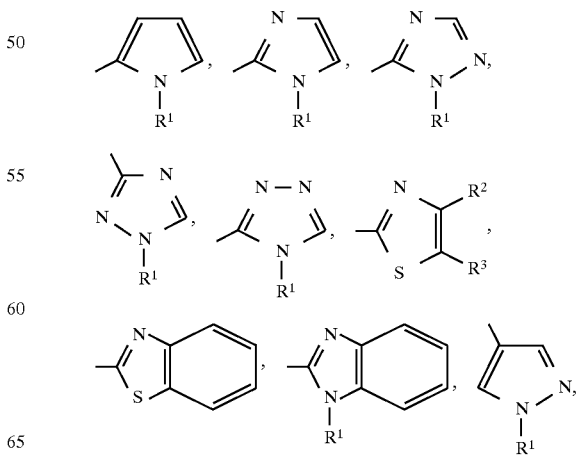

-continued

[chemical structures: furan, thiophene, or HO-C(CH3)=C(CH3)-pyrazole with N-CH3]

n is 1 and the chlorine atom is bonded to the 2- or 6-position of the pyridyl group or n is 2 and the chlorine atoms are bonded to the 2- and 6-position of the pyridyl group, $R^1$ is hydrogen or is $C_{1-4}$ alkyl, optionally substituted by one to three identical or different substituents selected from halogen, phenyl, cyano, $C_{1-4}$ alkoxy, $C_{1-4}$ alkylthio, $C_{1-4}$ alkylcarbonyl, $C_{1-4}$ alkoxycarbonyl, $C_{1-4}$ alkylaminocarbonyl, di($C_{1-4}$ alkyl)aminocarbonyl, hydroxyimino and $C_{1-4}$ alkoxyimino, or $R^1$ is $C_{2-4}$ alkenyl, optionally substituted by one to three identical or different substituents selected from halogen, $C_{1-4}$ alkoxy and $C_{1-4}$ alkoxycarbonyl, or $R^1$ is $C_{3-4}$ alkynyl, or $R^1$ is phenyl or pyrimidyl, which both can be substituted by one or two identical or different substituents selected from halogen, methoxy and ethoxy, and $R^2$ and $R^3$, independently of each other, are hydrogen or $C_{1-4}$ alkyl.

Particularly preferred chloropyridylcarbonyl derivatives of the formula (I) are those, in which Het is

[chemical structures: various heterocycles including pyrrole, pyrazole, triazole variants with $R^1$; and thiazole with $R^2$, $R^3$; benzothiazole, benzimidazole, pyrazole variants]

[chemical structures: furan, thiophene, or HO-C(CH3)=C(CH3)-pyrazole with N-CH3]

n is 1 and the chlorine atom is bonded to the 2- or 6-position of the pyridyl group or n is 2 and the chlorine atoms are bonded to the 2- and 6-position of the pyridyl group, $R^1$ is hydrogen or is $C_{1-4}$ alkyl, optionally substituted by one to three identical or different substituents selected from fluorine, chlorine, phenyl, cyano, methoxy, methylthio, methylcarbonyl, tert-butylcarbonyl, methoxycarbonyl, ethoxycarbonyl, methylainocarbonyl, ethylaminocarbonyl, dimethylaminocarbonyl, hydroxyimino and methoxyimino, or $R^1$ is $C_{2-4}$ alkenyl, optionally substituted by one to three identical or different substituents selected from fluorine, chlorine, methoxy and methoxycarbonyl, or $R^1$ is $C_{3-4}$ alkynyl, or $R^1$ is phenyl or pyrimidyl, which both can be substituted by one or two identical or different substituents selected from fluorine, chlorine and methoxy, and $R^2$ and $R^3$, independently of each other, are hydrogen or methyl.

Addition products of acids and those chloropyridylcarbonyl derivatives of the formula (I), in which Het and n have the meanings which have already been mentioned as preferred for this radical and this index, are also preferred compounds according to the invention.

The acids which can be added on include, preferably, hydrogen halide acids, such as, for example, hydrochloric acid and hydrobromic acid, in particular hydrochloric acid, and, furthermore, phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example p-toluenesulphonic acid, 1,5-naphthalenedisulphonic acid or camphorsulphonic acid, as well as saccharin and thiosaccharin.

Addition products of salts of metals of main groups II to IV and of sub-groups I and II and IV to VIII of the periodic table of the elements and those chloropyridylcarbonyl derivatives of the formula (I), in which Het an n have the meanings which have already been mentioned as preferred for this radical and this index, are also preferred compounds according to the invention.

Salts of copper, zinc, manganese, magnesium, tin, iron and nickel are particularly preferred here. Possible anions of these salts are those which are derived from those acids which lead to physiologically acceptable addition products. Particularly preferred acids of this type are, in this connection, the hydrogen halide acids, such as, for example, hydrochloric acid and hydrobromic acid, and, furthermore, phosphoric acid, nitric acid and sulphuric acid.

The substances listed in the following Table 1 may be mentioned as examples of chloropyridylcarbonyl derivatives of the formula (I). The heterocyclic radicals are identified by Q1 to Q12, which have the following meanings:

Q1 represents

[chemical structure: pyrrole with $R^1$]

Q2 represents

[chemical structure: pyrazole with $R^1$]

Q3 represents

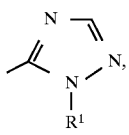

Q4 represents

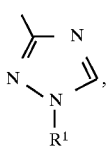

Q5 represents

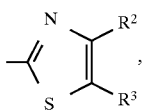

Q6 represents

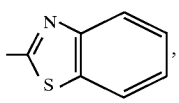

Q7 represents

Q8 represents

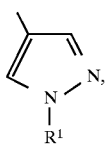

Q9 represents

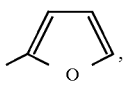

Q10 represents

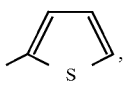

Q11 represents

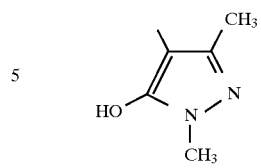

and Q12 represents

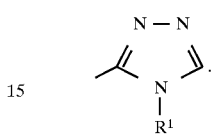

TABLE 1

| $(Cl)_n$ | Het | $R^1$, $R^2$ or $R^3$ |
|---|---|---|
| 2-Cl | Q2 | $R^1$: $CH_3$ |
| 2-Cl | Q3 | $R^1$: $CH_3$ |
| 2,6-$Cl_2$ | Q1 | $R^1$: H |
| 2,6-$Cl_2$ | Q2 | $R^1$: H |
| 2,6-$Cl_2$ | Q3 | $R^1$: H |
| 2,6-$Cl_2$ | Q4 | $R^1$: H |
| 2,6-$Cl_2$ | Q2 | $R^1$: $CH_3$ |
| 2,6-$Cl_2$ | Q3 | $R^1$: $CH_3$ |
| 2,6-$Cl_2$ | Q4 | $R^1$: $CH_3$ |
| 2,6-$Cl_2$ | Q4 | $R^1$: $C_2H_5$ |
| 2,6-$Cl_2$ | Q3 | $R^1$: $CH(CH_3)_2$ |
| 2,6-$Cl_2$ | Q3 | $R^1$: $CH_2CH_2CH_3$ |
| 2,6-$Cl_2$ | Q4 | $R^1$: $CH(CH_3)_2$ |
| 2,6-$Cl_2$ | Q2 | $R^1$: $CH_2OCH_3$ |
| 2,6-$Cl_2$ | Q3 | $R^1$: $CH_2OCH_3$ |
| 2,6-$Cl_2$ | Q4 | $R^1$: $CH_2OCH_3$ |
| 2,6-$Cl_2$ | Q4 | $R^1$: $CH_3SCH_3$ |
| 2,6-$Cl_2$ | Q2 | $R^1$: $CH_2COOCH_3$ |
| 2,6-$Cl_2$ | Q4 | $R^1$: $CH_2COOCH_3$ |
| 2,6-$Cl_2$ | Q3 | $R^1$: $CH_2COC(CH_3)_3$ |
| 2,6-$Cl_2$ | Q2 | $R^1$: $CH(CH_3)_2$ |
| 2,6-$Cl_2$ | Q2 | $R^2$: $CH_2CON(CH_3)_2$ |
| 2,6-$Cl_2$ | Q2 | $R^1$: $CH_2CH_2CON(CH_3)_2$ |
| 2,6-$Cl_2$ | Q2 | $R^1$: $CH_2CONHC_2H_5$ |
| 2,6-$Cl_2$ | Q2 | $R^1$: $CH_2CH_2CONHCH_3$ |
| 2,6-$Cl_2$ | Q2 | $R^1$: $CH_2C_6H_5$ |
| 2,6-$Cl_2$ | Q2 | $R^1$: $CH_2CH_2CH=CH_2$ |
| 2,6-$Cl_2$ | Q2 | $R^1$: $CH_2CH_2CH=NOCH_3$ |
| 2,6-$Cl_2$ | Q2 | $R^1$: $CH_2CH=CH_2$ |
| 2,6-$Cl_2$ | Q4 | $R^1$: $CH_2CH=CH_2$ |
| 2,6-$Cl_2$ | Q2 | $R^1$: $CH=CH_2$ |
| 2,6-$Cl_2$ | Q3 | $R^1$: $CH=CH_2$ |
| 2,6-$Cl_2$ | Q2 | $R^1$: $CH_2C\equiv CH$ |
| 2,6-$Cl_2$ | Q2 | $R^1$: $CH_2CH=NOCH_3$ |
| 2,6-$Cl_2$ | Q2 | $R^1$: $CH_2CH_2=NOH$ |
| 2,6-$Cl_2$ | Q2 | $R^1$: $CH_2CH=NOH$ |
| 2,6-$Cl_2$ | Q2 | $R^1$: $CH_2CH_2CH=NOCH_3$ |
| 2,6-$Cl_2$ | Q2 | $R^1$: $CH_2CN$ |
| 2,6-$Cl_2$ | Q4 | $R^1$: $CH_2CN$ |
| 2,6-$Cl_2$ | Q2 | $R^1$: $CH(CH_3)CN$ |
| 2,6-$Cl_2$ | Q2 | $R^1$: $CH_2CH_2CN$ |
| 2,6-$Cl_2$ | Q4 | $R^1$: $CH_2CH_2CN$ |
| 2,6-$Cl_2$ | Q2 | $R^1$: $CH_2CCl=CH_2$ |
| 2,6-$Cl_2$ | Q2 | $R^1$: $CH_2CH_2CF=CF_2$ |
| 2,6-$Cl_2$ | Q2 | $R^1$: $CH(CH_3)COOC_2H_5$ |
| 2,6-$Cl_2$ | Q2 | $R^1$: $CH_2CF_3$ |
| 2,6-$Cl_2$ | Q2 | $R^1$: $CHF_2$ |
| 2,6-$Cl_2$ | Q4 | $R^1$: $CHF_2$ |

TABLE 1-continued (Cl)ₙ—[pyridine ring]—C(=O)—Het (I)

| (Cl)ₙ | Het | $R^1$, $R^2$ or $R^3$ |
|---|---|---|
| 2,6-Cl₂ | Q2 | $R^1$: CF₃ |
| 2,6-Cl₂ | Q3 | $R^1$: CF₃ |
| 2,6-Cl₂ | Q2 | $R^1$: C₆H₅ |
| 2,6-Cl₂ | Q3 | $R^1$: C₆H₅ |
| 2,6-Cl₂ | Q2 | $R^1$: 4,6-dimethyl-pyrimidin-2-yl |
| 2,6-Cl₂ | Q2 | $R^1$: C(=CHOCH₃)-COOCH₃ |
| 2,6-Cl₂ | Q2 | $R^1$: CH₂COCH₃ |
| 2,6-Cl₂ | Q5 | $R^2$: H, $R^3$: H |
| 2,6-Cl₂ | Q5 | $R^2$: CH₃, $R^3$: H |
| 2,6-Cl₂ | Q5 | $R^2$: H, $R^3$: CH₃ |
| 2,6-Cl₂ | Q5 | $R^2$: CH₃, $R^3$: CH₃ |
| 2,6-Cl₂ | Q6 | |
| 2,6-Cl₂ | Q7 | $R^1$: H |
| 2,6-Cl₂ | Q7 | $R^1$: CH₃ |
| 2,6-Cl₂ | Q8 | $R^1$: CH₃ |
| 2,6-Cl₂ | Q9 | |
| 2,6-Cl₂ | Q10 | |
| 2,6-Cl₂ | Q11 | |
| 2,6-Cl₂ | Q12 | $R^1$: CH₃ |

If 2,6-dichloroisonicotinic acid chloride and 1-methyl-1,2,4-triazole are used as starting materials, the course of process (a) according to the invention can be illustrated by the following formula scheme:

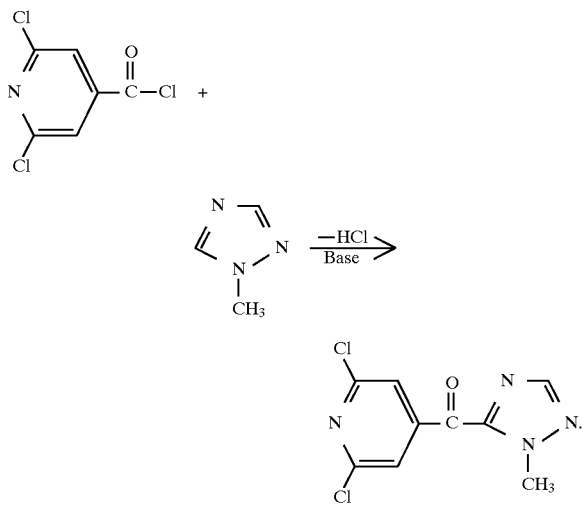

If 5-(2',6'-dichloro-4'-pyridylcarbonyl)-1-ethenyl-1,2,4-triazole is used as starting material and sodium periodate in the presence of osmium(IV)oxide is used as oxidizing agent, the course of process (b) according to the invention can be illustrated by the following formula scheme:

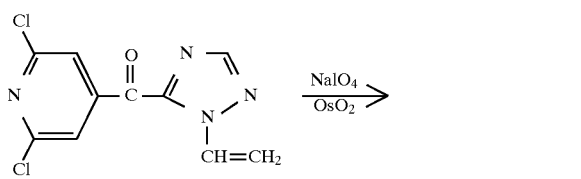

If 2-(2',6'-dichloro-4'-pyridylcarbonyl)-imidazole and isopropyl-bromide are used as starting materials, the course of process (c) according to the invention can be illustrated by the following formula scheme:

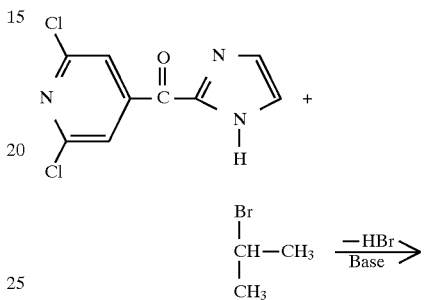

Formula (II) provides a general definition of the chloropyridylcarbonyl halides required as starting materials for carrying out process (a) according to the invention. In this formula, n preferably is 1 or 2, and Hal preferably represents chlorine or bromine.

As examples of compounds of the formula (II), there may be mentioned 2-chloroisonicotinic acid chloride, 2-chloroisonicotinic acid bromide, 2,6-dichloroisonicotinic acid chloride and 2,6-dichloroisonicotinic acid bromide.

The chloropyridylcarbonyl halides of the formula (II) are known.

Formula (III) provides a general definition of the heterocycles which are required as reaction components for carrying out process (b) according to the invention. In this formula $Het^1$ preferably is

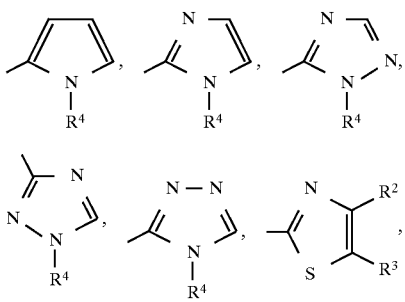

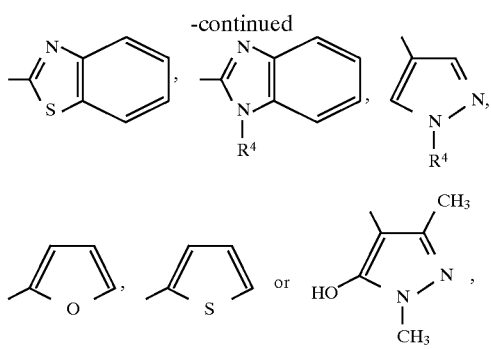

in which
- $R^2$ and $R^3$, independently of each other, preferably are hydrogen or $C_{1-4}$ alkyl and
- $R^4$ preferably is $C_{1-4}$ alkyl optionally substituted by one to three identical or different substituents selected from halogen, phenyl, cyano, $C_{1-4}$ alkoxy, $C_{1-4}$ alkylthio, $C_{1-4}$ alkylcarbonyl, $C_{1-4}$ alkoxycarbonyl, $C_{1-4}$ alkylaminocarbonyl, di($C_{1-4}$ alkyl)aminocarbonyl, hydroxyimino and $C_{1-4}$ alkoxyimino, or
- $R^4$ is $C_{2-4}$ alkenyl, optionally substituted by one to three identical or different substitutuents selected from halogen, $C_{1-4}$ alkoxy and $C_{1-4}$ alkoxycarbonyl, or
- $R^4$ is $C_{3-4}$ alkynyl, or
- $R^4$ is phenyl or pyrimidyl, which both can be substituted by one or two identical or different substituents selected from halogen, methoxy and ethoxy.

Het$^1$ particularly preferably is

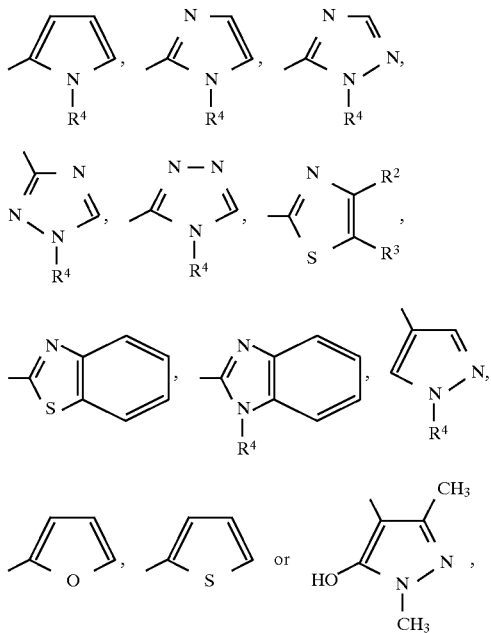

in which
- $R^2$ and $R^3$, independently of each other, particularly preferably are hydrogen or methyl and
- $R^4$ particularly preferably is $C_{1-4}$ alkyl, optionally substituted by one to three identical or different substituents selected from fluorine, chlorine, phenyl, cyano, methoxy, methylthio, methylcarbonyl, tert-butylcarbonyl, methoxycarbonyl, ethoxycarbonyl, methylaminocarbonyl, ethylaminocarbonyl, dimethylaminocarbonyl, hydroxyimino and methoxyimino, or
- $R^4$ is $C_{2-4}$ alkenyl, optionally substituted by one to three identical or different substituents selected from fluorine, chlorine, methoxy and methoxycarbonyl, or
- $R^4$ is $C_{3-4}$ alkynyl, or
- $R^4$ is phenyl or pyrimidyl, which both can be substituted by one or two identical or different substituents selected from fluorine, chlorine and methoxy.

The following compounds may be mentioned as examples of heterocycles of the formula (III):

1-Methylpyrrole, 1-isopropylpyrrole, 1-methylimidazole, 1-methoxymethylimidazole, 1-isopropylimidazole, 1-cyanomethylimidazole, 1-(2-cyanoethyl)-imidazole, 1-allylimidazole, 1-difluoromethylimidazole, 1-trifluoromethylimidazole, 1-phenylimidazole, 1-methyl-1,2,4-triazole, 1-ethyl-1,2,4-triazole, 1-isopropyl-1,2,4-triazole, 1-n-propyl-1,2,4-triazole, 1-(methoxycarbonylmethyl)-imidazole, 1-(ethoxycarbonylmethyl)-imidazole, 1-{2-(methoxycarbonyl)ethyl}imidazole, 1-{1-(ethoxycarbonyl)-ethyl}-imidazole, 1-{2-(ethoxycarbonyl)-ethyl}-imidazole, 1-(dimethylaminocarbonylmethyl)-imidazole, 1-{2-(dimethylaminocarbonyl)-ethyl}-imidazole, 1-(4,6-dimethoxypyrimidin-2-yl)-imidazole, 1,3-dimethyl-5-hydroxypyrazole, thiazole, 4-methylthiazole, 5-methylthiazole, 4,5-dimethylthiazole, benzothiazole, furan and thiophene.

The heterocycles of the formula (III) are known.

Formula (Ia) provides a general definition of the chloropyridylcarbonyl derivatives, which are required as starting materials for carrying out process (b) according to the invention. In this formula, n preferably is 1 or 2, and Het$^2$ preferably represents a group of the formula

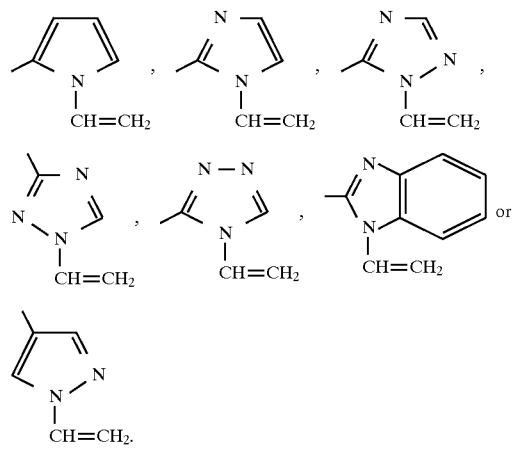

The following compounds may be mentioned as examples of chloropyridylcarbonyl derivatives of the formula (Ia):

1-Vinyl-2-(2'-chloro-4'-pyridylcarbonyl)pyrrole, 1-vinyl-2-(2',6'-dichloro-4'-pyridylcarbonyl)-pyrrole, 1-vinyl-2-(2'-chloro-4'-pyridylcarbonyl)-imidazole, 1-vinyl-2-(2',6'-di-chloro-4'-pyridylcarbonyl)-imidazole, 1-vinyl-5-(2'-chloro-4'-pyridylcarbonyl)-1,2,4-triazole, 1-vinyl-5-(2',6'-dichloro-4'-pyridylcarbonyl)-1,2,4-triazole, 1-vinyl-2-(2'-chloro-4'-pyridyl-carbonyl)-benzodiazole, 1-vinyl-2-(2',6'-dichloro-4'-pyridylcarbonyl)benzodiazole, 1-vinyl-4-(2',6'- dichloro-4'-pyridylcarbonyl)pyrazole, 1-vinyl-4-(2'-chloro-4'-pyridyl- carbonyl)-pyrazole.

The chloropyridylcarbonyl derivatives of the formula (Ia) can be prepared by process (a) according to the invention.

In carrying out process (b) according to the invention, periodic acid or their customary salts can be used as oxidizing agents in the presence of osmium (IV) oxide. Examples of such oxidizing agents are periodic acid and sodium periodate. Formula (Ib) provides a general definition of the chloropyridylcarbonyl derivatives, which are required as starting materials for carrying out process (c) according to the invention. In this formula, n preferably is 1 or 2, and Het³ preferably represents a group of the formula

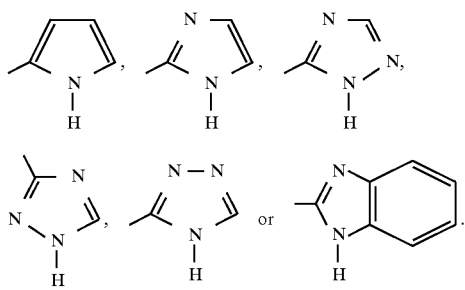

The following compounds may be mentioned as examples of chloropyridylcarbonyl derivatives of the formula (Ib):

2-(2'-Chloro-4'-pyridylcarbonyl)-pyrrole, 2-(2',6'-dichloro-4'-pyridylcarbonyl)-pyrrole, 2-(2'-chloro-4'-pyridylcarbonyl)imidazole, 2-(2',6'-di-chloro-4'-pyridylcarbonyl)-imidazole, 5-(2'-chloro-4'-pyridylcarbonyl)-1,2,4-triazole, 5-(2',6'-dichloro-4'-pyridylcarbonyl)-1,2,4-triazole, 2-(2'-chloro-4'-pyridylcarbonyl)-benzodiazole, 2-(2',6'-dichloro-4'-pyridyl-carbonyl)-benzodiazole, 4-(2',6'-dichloro-4'-pyridylcarbonyl)-pyrazole and 4-(2'-chloro-4'-pyridyl-carbonyl)-pyrazole.

The chloropyridylcarbonyl derivatives of the formula (Ib) can be prepared by process (b) according to the invention.

Formula (IV) provides a general definition of the halogeno compounds, which are required as reaction components for carrying out process (c) according to the invention. In this formula, R⁴ preferably has those meanings, which have already been mentioned as preferred for this substituent. Hal¹ preferably is chlorine or bromine.

The following compounds may be mentioned as examples of halogeno compounds of the formula (IV):

Isopropyl bromide, methyl bromide, methoxymethyl bromide, benzyl bromide, chloroacetonitrile, 3-chloroacetonitrile, allyl bromide, propargyl bromide, methyl chloroacetate, methyl 3-chloroacetate, ethyl chloroacetate, ethyl 3-chloroacetate, ethyl 3-chloropropionate, ethyl 2-chloropropionate and N,N-dimethyl chloroacetamide, N,N-dimethyl 3-chloropropionamide.

The halogeno compounds of the formula (IV) are known or can be prepared according to known processes.

All inert organic solvents customary for such reactions can be used as diluents in carrying out process (a) according to the invention. The following solvents can preferably be used: Aliphatic, alicyclic and aromatic hydrocarbons, which may be chlorinated, such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers, such as diethyl ether, methyl ethyl ether, diisopropyl ether, dibutyl ether, dioxane, dimethoxyethane (DME), tetrahydrofurane (THF) and dimethylene glycol dimethyl ether; ketones, such as acetone, methylethyl ketone (MEK), methyl-iso-propyl ketone and methyl-iso-butyl ketone (MIBK); nitriles, such as acetonitrile and propionitrile; esters, such as ethyl acetate and amyl acetate; acid amides, such as dimethyl formamide (DMF), dimethyl acetamide (DMA), N-methylpyrrolidone, 1,3-dimethyl-2-imidazolidinone and hexamethylphosphoric triamide (HMPA); sulfones and sulfoxides, such as dimethyl sulfoxide (DMSO) and sulfolane; bases, such as pyridine, and also nitromethane.

Process (a) can be carried out in the presence of an acid binder and a catalyst, if heterocycles of the formula (III) are used, in which Het¹ represents an imidazolyl group, a 1,2,4-triazolyl, thiazolyl, benzothiazolyl or a benzoimidazolyl group. Suitable acid binders are organic bases, for example tertiary amines, dialkylaminoanilines and pyridines, such as triethylamine, 1,1,4,4-tetramethyl-ethylenediamine (TMEDA), N,N-dimethylaniline, N,N-diethylaniline, pyridine, 4-dimethylaminopyridine (DMAP), 1,4-diazabicyclo[2,2,2]octane (DABCO) and 1,8-diazabicyclo-[5,4,0]undec-6-ene (DBU). Examples of suitable catalysts are: quaternary ammonium salts, such as tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide and benzyltriethylammonium chloride; and crown ethers, such as dibenzo-18-crown-6, dicyclohexyl-18-crown-6,18-crown-6, [2,2,2]-cryptate, [2,1,1]-cryptate, [2,2,1]-cryptate, [2,2,B]-cryptate and [3,2,2]-cryptate.

Process (a) can be carried out in the presence of a Lewis acid as a catalyst, if heterocycles of the formula (III) are used, in which Het¹ represents a thienyl, furyl or pyrrolyl group. Examples of suitable Lewis acids are:

Aluminium chloride, antimony(V) chloride, iron(III) chloride, tin(IV) chloride, titanium(IV) chloride, zinc chloride, hydrogen fluoride, boron trifluoride, phosphoric acid and polyphosphoric acid.

In carrying out process (a) according to the invention, the reaction temperatures can be varied within a substantially wide range. The reaction is generally carried out at a temperature between about −76° C. and about +150° C., preferably between 0° C. and about 120° C.

Process (a) according to the invention is generally carried out under atmospheric pressure but, if desired, can also be carried out under elevated or reduced pressure.

In carrying out process (a) according to the invention, in general 1 mol of chloropyridylcarbonyl halide of the formula (II) is reacted with 0.1 to 10 mol of a heterocycle of the formula (III) in the presence of a diluent and, if appropriate, in the presence of an acid binder and/or a catalyst. Working up is carried out by customary methods.

All inert organic solvents customary for such reactions can be used as diluents in carrying out process (b) according to the invention. The following solvents can preferably be used: Aliphatic, alicyclic and aromatic hydrocarbons, which may be chlorinated, such as pentane, hexane, cyclohexane, petroleum ether, ligroin, benzene, toluene, xylene, dichloromethane, chlorobenzene and dichlorobenzene; ethers, such as diethyl ether, methyl ethyl ether, diisopropyl ether, dibutyl ether, dioxane, dimethoxyethane (DME), tetrahydrofurane (THF) and dimethylene glycol dimethyl ether; ketones, such as acetone, methylethyl ketone (MEK), methyl-iso-propyl ketone and methyl-iso-butyl ketone (MIBK); nitriles, such as acetonitrile and propionitrile; alcohols, such as methanol, ethanol, isopropanol, butanol and ethylene glycol; esters, such as ethyl acetate and amyl acetate; acid amides, such as dimethyl formamide (DMF), dimethyl acetamide (DMA), N-methylpyrrolidone, 1,3-dimethyl-2-imidazolidinone and hexamethylphosphoric triamide (HMPA); sulfones and sulfoxides, such as dimethyl sulfoxide (DMSO) and sulfolane; and also bases, such as pyridine. It is also possible to use a mixture of water and a water-miscible organic solvent, such as dioxane, as a diluent.

In carrying out process (b) according to the invention, the reaction temperatures can be varied within a substantially wide range. The reaction is generally carried out at a temperature between about −70° C. and about +150° C., preferably between 20° C. and about 120° C.

Process (b) according to the invention is generally carried out under atmospheric pressure but, if desired, can also be carried out under elevated or reduced pressure.

In carrying out process (b) according to the invention, in general 1 mol of chloropyridylcarbonyl derivative of the formula (Ia) is reacted with 2 to 20 mol of periodic acid or a salt thereof in the presence of osmium(IV)oxide and in the presence of a diluent. Working up is carried out by customary methods.

All inert organic solvents customary for such reactions can be used as diluents in carrying out process (c) according to the invention. The following solvents can preferably be used: Aliphatic, alicyclic and aromatic hydrocarbons, which may be chlorinated, such as pentane, hexane, cyclohexane, petroleum ether, ligroin, benzene, toluene, xylene, dichloromethane, chloroform, carbon tetrachloride, 1,2-dichloroethane, chlorobenzene and dichlorobenzene; ethers, such as ethyl ether, methyl ethyl ether, isopropyl ether, butyl ether, dioxane, dimethoxyethane (DME), tetrahydrofuran (THF) and diethylene glycol dimethyl ether (DGM); nitriles, such as acetonitrile and propionitrile; alcohols, such as methanol, ethanol, isopropanol, butanol and ethylene glycol; esters, such as ethyl acetate and amyl acetate; acid amides, such as dimethylformamide (DMF), dimethylacetamide (DMA), N-methylpyrrolidone, 1,3-dimethyl-2-imidazolidinone and hexamethylphosphoric triamide (HMPA); sulfones and sulfoxides, such as dimethyl sulfoxide (DMSO) and sulfolan; and bases, such as pyridine.

Suitable acid-binders for carrying out process (c) according to the invention are customary organic bases. Examples of preferred acid-binders are tertiary amines, dialkylaminoanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo [2,2,2] octane (DABCO) and 1,8-diazabicyclo[5,4,0]undec-6-ene (DBU).

Process (c) according to the invention can be carried out in the presence of a catalyst which is customary for such type of reaction. As examples of catalysts which can preferably be used, there may be mentioned quaternary ammonium salts, such as tetramethylammonium bromide, tetrapropylammonium bromide, tetrabutylammonium bromide, tetrabutylammonium bissulfate, tetrabutylammonium iodide, trioctylmethylammonium chloride, benzyltriethylammonium bromide, butylpyridinium bromide, heptylpyridinium bromide and benzyltriethylammonium chloride; and crown ethers, such as dibenzo-18-crown-6, dicyclohexyl-18-crown-6, 18-crown-6, [2,2,2]-cryptate, [2,1,1]-cryptate, [2,2,1]-cryptate, [2,2,B]-cryptate and [3,2,2]-cryptate.

In carrying out process (c) according to the invention, the reaction temperatures can be varied within a substantially wide range. The reaction is generally carried out at a temperature between about −76° C. and about +150° C., preferably between 0° C. and about 120° C.

Process (c) according to the invention is generally carried out under atmospheric pressure but, if desired, can also be carried out under elevated or reduced pressure.

In carrying out process (c) according to the invention, in general 1 mol of chloropyridylcarbonyl derivative of the formula (Ib) is reacted with 0.1 to 10 mol of a halogeno compound of the formula (IV) in the presence of a diluent and, if appropriate, in the presence of an acid-binder and of a catalyst. Working up is carried out by customary methods.

The chloropyridylcarbonyl derivatives of the formula (I) can be converted into acid addition salts or metal salt complexes.

Those acids which have already been mentioned as preferred acids in connection with the description of the acid addition salts according to the invention can preferably be used to prepare acid addition salts of the compounds of the formula (I).

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Those salts of metals which have already been mentioned as preferred metal salts in connection with the description of the metal salt complexes according to the invention can preferably be used to prepare metal salt complexes of the compounds of the formula (I).

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purificated by recrystallization.

The compounds according to the present invention exhibit a strong microbicidal activity and thus can be used for combating undesired microorganisms, such as phytopathogenic fungi and bacteriae, in agriculture and horticulture. The compounds are suitable for the direct control of undesired microorganisms as well as for generating resistance in plants against attack be undesirable microorganisms.

Resistance-inducing substances in the present connection are to be understood as those substances which are capable of stimulating the defence system of plants such that the treated plants, when subsequently inoculated with undesirable microorganisms, display substantial resistance to these microorganisms.

Undesirable microorganisms in the present case are to be understood as phytopathogenic fungi and bacteria. The substances according to the invention can thus be employed to generate resistance in plants against attack by the harmful organisms mentioned within a certain period of time after the treatment. The period of time within which resistance is brought about in general extends from 1 to 10 days, preferably 1 to 7 days, after treatment of the plants with the active compounds.

Generally, the compounds according to the invention can be used as fungicides for combating phytopathogenic fungi, such as Plasmodiophoromycetes, Oomycetes, Chytridiomycetes, Zygomycetes, Ascomycetes, Basidiomycetes and Deuteromycetes, and can also be used as bactericides for combating bacteriae, such as Pseudomonoadaceae, Rhizobiaceae, Enterobacteriaceae, Corynebacteriaceae and Streptomycetaceae.

Some causative organisms of fungal and bacterial diseases included under the abovementioned main headings, are mentioned below as non-limiting examples: Xanthomonas species, such as, for example, *Xanthomonas campestris pv.oryzae;* Pseudomonas species, such as, for example, *Pseudomonas syringae pv.lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora cubensis;* Plasmopara species, such as, for example, *Plasmopara viticola;* Peronospora species, such as, for example, *Peronospora pisior pv.brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teresor P. graminea;* (Conidial form: Drechslera, Synonym: Helminthosporium); Cochliobolus species, such as, for example, *Cochliobolus sativus;* (Conidial form: Drechslera, Synonym: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nudaor, Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dye stuffs, azo dye stuffs or metal phthalocyanine dye stuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared there from by further dilution, such as ready-to-use solutions, emulsions, suspensions, powders, pastes and granules. They are used in the customary manner, for example by watering, immersion, spraying, atomising, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

EXAMPLES

Synthesis Example 1

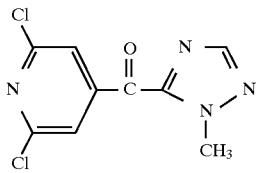

Pyridine (4.4 g) was added to a dichloromethylene (300 ml) solution of 1-methyl-1,2,4-triazole (4.15 g), and 2,6-dichloroisonicotinic acid chloride (10.6 g) was dropwisely added thereto under stirring while cooling with ice. The reaction mixture was stirred at a room temperature for 8 hours. After finishing the reaction, the reaction mixture was washed successively with an aqueous 3% hydrochloric acid solution, an aqueous 3% sodium hydroxide solution and water. The organic layer was then dried over anhydrous sodium sulfate. The organic layer was concentrated under reduced pressure, and the remaining residue was purified by silica gel column chromatography (elution solvent: chloroform). 5-(2',6'-Dichloro-4'-pyridylcarbonyl)-1-methyl-1,2,4-triazole (4.7 g) were obtained in this manner.

Melting point: 130.5°–131.5° C.

Synthesis Example 2

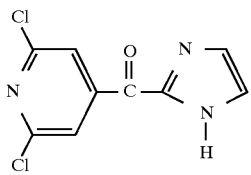

Triethylamine (5.1 g) was added to a pyridine (10 ml) solution of imidazole (1.7 g), and 2,6-dichloroisonicotinic acid chloride (10.6 g) was dropwisely added thereto under stirring at 0°–10° C. The reaction mixture was stirred at a room temperature for 3 hours. Thereafter, an aqueous 7.5-N sodium hydroxide solution was added to the reaction mixture and the mixture was heated under refluxing for 1 hour. After finishing the reaction, water was added and the reaction mixture was cooled. The crystals which precipitated were collected by filtration. 2-(2',6'-Dichloro-4'-pyridylcarbonyl)-imidazole (5.2 g) were obtained in this manner.

Melting point: 173.5°–175° C.

Synthesis Example 3

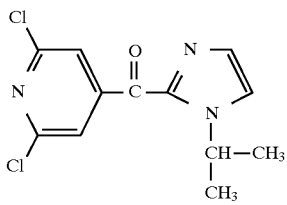

Anhydrous potassium carbonate (1.5 g) and isopropyl bromide (1.23 g) were added to an acetonitrile (50 ml) solution of 2-(2',6'-dichloro-4'-pyridylcarbonyl)-imidazole (2.42 g), and the mixture was heated under refluxing for 6 hours. After finishing the reaction, water was added thereto followed by extraction with methylene chloride. The organic layer was dried over anhydrous sodium sulfate, concentrated under reduced pressure, and the remaining residue was purified by silica gel column chromatography (elution solvent: chloroform). 2-(2',6'-Dichloro-4'-pyridylcarbonyl)-1-isopropylimidazole (1.8 g) were obtained in this manner.

$n_D^{20}$=1.5820.

Synthesis Example 4

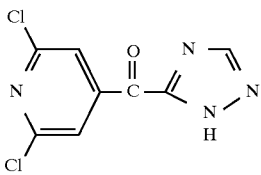

5-(2',6'-Dichloropyridylcarbonyl)-1-vinyl-1,2,4-triazole (2.69 g) was added to a solution of sodium periodate (4.3 g) and osmium(IV)oxide (0.05 g) in a mixture of dioxane (70 ml) and water (20 ml) at room temperature with stirring. The mixture was stirred overnight at room temperature. After finishing the reaction, water was added thereto followed by extraction with methylene chloride. The organic layer was dried over anhydrous sodium sulfate, concentrated under reduced pressure, and the remaining residue was purified by silica gel column chromatography (elution solvent:chloroform). 3-(2',6'-Dichloro-4'-pyridylcarbonyl)-1,2,4-triazole (1.7 g) were obtained in this manner.

Melting point: 155°–158° C.

Synthesis Example 5

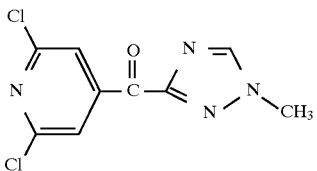

Anhydrous potassium carbonate (1.5 g) and methyl iodide (1.4 g) were added to an acetonitrile (50 ml) solution of 3-(2',6'-dichloropyridylcarbonyl)-1,2,4-triazole (2.41 g), and the mixture was heated under refluxing for 6 hours. After finishing the reaction, water was added thereto followed by extraction with methylene chloride. The organic layer was dried over anhydrous sodium sulfate, concentrated under reduced pressure, and the remaining residue was purified by silica gel column chromatography (elution solvent:chloroform). 3-(2',6'-Dichloro-4'-pyridylcarbonyl)-1-methyl-1,2,4-triazole (1.5 g) were obtained in this manner.

Melting point: 203°–206° C.

Synthesis Example 6

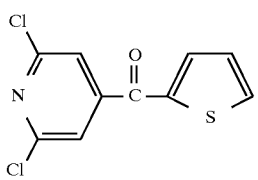

Anhydrous tin(IV) chloride (2.6 g) was added to a nitromethane (30 ml) solution of 2,6-dichloropyrimidine-4-carbonyl chloride (2.1 g) and thiophene (3 g) at room temperature. The mixture was heated under refluxing for 5 hours. After finishing the reaction, the mixture was poured into ice-water (50 g) and hydrochloric acid (10 ml), followed by extraction with methylene chloride (50 ml×3). The organic layer was washed with water, followed by drying over anhydrous sodium sulfate. After distilling off the solvent, the crude product was purified by silica gel column chromatography (elution solvent:toluene/chloroform=1/1). 2-(2',6'-Dichloro-4'-pyridylcarbonyl)-thiophen (1 g) were obtained in this manner.

Melting point: 129°–130° C.

The following Table 2 shows compounds of the formula (I), which were synthesized according to the processes mentioned above. The heterocyclic radicals in this Table 2 are identified in the same manner as in Table 1.

TABLE 2

$(Cl)_n$-pyridyl-C(=O)-Het (I)

| Compound No. | $(Cl)_n$ | Het | $R^1$, $R^2$ or $R^3$ | Melting point or refractive index |
|---|---|---|---|---|
| 1  | 2,6-$Cl_2$ | Q2 | $R^1$: H                | 173.5–175° C. |
| 2  | 2-Cl       | Q2 | $R^1$: $CH_3$           | 238–239° C. |
| 3  | 2,6-$Cl_2$ | Q1 | $R^1$: $CH_3$           | 143–144° C. |
| 4  | 2,6-$Cl_2$ | Q2 | $R^1$: $CH_3$           | 185–186° C. |
| 5  | 2,6-$Cl_2$ | Q3 | $R^1$: $CH_3$           | 130.5–131.5° C. |
| 6  | 2,6-$Cl_2$ | Q3 | $R^1$: $CH_3$           | 76–78° C. |
| 7  | 2,6-$Cl_2$ | Q4 | $R^1$: $CH_3$           | 203–206° C. |
| 8  | 2,6-$Cl_2$ | Q4 | $R^1$: $C_2H_5$         | 123–124° C. |
| 9  | 2,6-$Cl_2$ | Q4 | $R^1$: $CH_2CH_2CH_3$   | 147–150° C. |
| 10 | 2,6-$Cl_2$ | Q4 | $R^1$: $CH(CH_3)_2$     | 100–103° C. |
| 11 | 2,6-$Cl_2$ | Q2 | $R^1$: $CH(CH_3)_2$     | $n_D^{20}$ = 1.5820 |
| 12 | 2,6-$Cl_2$ | Q3 | $R^1$: $CH(CH_3)_2$     | 92–93.5° C. |
| 13 | 2,6-$Cl_2$ | Q2 | $R^1$: $CH=CH_2$        | 178–179° C. |
| 14 | 2,6-$Cl_2$ | Q2 | $R^1$: $CH_2CH=CH_2$    | 94–95° C. |
| 15 | 2,6-$Cl_2$ | Q3 | $R^1$: $CH_2CH=CH_2$    | $n_D^{20}$ = 1.5729 |
| 16 | 2,6-$Cl_2$ | Q2 | $R^1$: $CH_2CN$         | 130–131° C. |
| 17 | 2,6-$Cl_2$ | Q4 | $R^1$: $CH_2CN$         | $n_D^{20}$ = 1.5367 |
| 18 | 2,6-$Cl_2$ | Q2 | $R^1$: $CH_2CH_2CN$     | amorphous |
| 19 | 2,6-$Cl_2$ | Q2 | $R^1$: $CH_2OCH_3$      | 79–82° C. |
| 20 | 2,6-$Cl_2$ | Q3 | $R^1$: $CH_2OCH_3$      | 89–94° C. |
| 21 | 2,6-$Cl_2$ | Q4 | $R^1$: $CH_2OCH_3$      | 193–194° C. |
| 22 | 2,6-$Cl_2$ | Q4 | $R^1$: $CH_2SCH_3$      | 151–152° C. |
| 23 | 2,6-$Cl_2$ | Q3 | $R^1$: $CH_2COC(CH_3)_3$ | $n_D^{20}$ = 1.5280 |
| 24 | 2,6-$Cl_2$ | Q2 | $R^1$: $CH_2-C_6H_5$    | amorphous |
| 25 | 2,6-$Cl_2$ | Q2 | $R^1$: $CHF_2$          | 95–96° C. |
| 26 | 2,6-$Cl_2$ | Q2 | $R^1$: $C_6H_5$         | amorphous |
| 27 | 2,6-$Cl_2$ | Q3 | $R^1$: $C_6H_5$         | 126.5–128° C. |
| 28 | 2,6-$Cl_2$ | Q2 | $R^1$: $CH_2CO_2CH_3$   | 144–145.5° C. |
| 29 | 2,6-$Cl_2$ | Q2 | $R^1$: $C(CH_2OCH_3)=CHOCH_3$ | $n_D^{°}$ = 1.5754 |
| 30 | 2,6-$Cl_2$ | Q2 | $R^1$: 4,6-dimethoxy-pyrimidin-2-yl | 147–148° C. |
| 31 | 2,6-$Cl_2$ | Q10 | —                      | 129–130° C. |

Use Example 1

Test of foliar spray effect against rice blast

Preparation of Formulations of the Compounds Tested

Active compound: 30–40 parts by weight

Carrier: mixture of diatomaceous earth and kaolin (1:5), 55–65 parts by weight

Emulsifier: polyoxyethylene alkyl phenyl ether, 5 parts by weight

Each of the wettable powders is prepared by pulverizing and mixing the above amounts of active compound, carrier and emulsifier. A portion of the wettable powder containing the prescribed amount of the active compound is diluted with water to be subjected to the test mentioned below.

Testing Procedure

Seedlings of paddy rice (cultivar: Kusabue) were cultured in vinyl pots each having a diameter of 6 cm. The previously prepared dilution of the prescribed concentration of active compound was sprayed at a rate of 25 ml per 3 pots over the foliage of the seedlings in the 1.5 leaf stage. 10 days after the application, a suspension of artificially cultured *Pyricularia oryzae* spores was spray-inoculated once on the seedlings, and the seedlings were maintained at 25° C. and 100% relative humidity for infection. 7 days after the inoculation, the infection degree per pot was examined and rated according to the following criteria. Further, the control value (%) was calculated. Furthermore, the phytotoxicity was concurrently examined The results are shown in the later-described Table 3. The data in Table 3 are average values of the results of 3 pots in one plot.

| Infection degree | Percentage of lesion area (%) | Infection degree | Percentage of lesion area (%) |
|---|---|---|---|
| 0   | 0             | 3 | 10–less than 20 |
| 0.5 | less than 2   | 4 | 20–less than 40 |
| 1   | 2–less than 5 | 5 | not less than 40 |
| 2   | 5–less than 10 |  |  |

Control value (%) = (1 − (infection degree in treated plot ÷ infection degree in non-treated plot)) × 100

Note:
The methods of evaluation of the infection degree and calculation of the control value were the same in Use Examples 1–4.

Use Example 2
Test of water surface application effect against rice blast

Testing Procedure

Seedlings of paddy rice (cultivar: Kusabue) in the 1.5 leaf stage were transplanted into irrigated plastic pots (100 cm²), one seedling per pot. 7 days after the transplanting (when the seedlings were in the 3–4 leaf stage), the dilution of the prescribed concentration of the active compound, which had been prepared in the manner similar to that of the above Use Example 1, was dropped at a rate of 10 ml per pot, with a pipette, to the water surface. 20 days after the chemical treatment, a suspension of artificially cultured rice blast (blast fungus race C) spores was spray-inoculated once on the seedlings, and the seedlings were incubated in the inoculation box at 25° C. and 100% relative humidity for 12 hours for infection. Thereafter, the seedlings were transferred to the greenhouse for management. 10 days after the inoculation, the infection degree per pot was evaluated, and the control value (%) was calculated. Furthermore, the phytotoxicity was concurrently examined. The results are shown in the later-described Table 3.

Use Example 3
Test of foliar spray against tomato late blight

Preparation of Formulations of the Active Compounds Tested

Active Compound: 30–40 parts by weight
Carrier: mixture of diatomaceous earth and kaolin (1:5), 55–65 parts by weight
Emulsifier: polyoxyethylene alkyl phenyl ether, 5 parts by weight Wettable powders are prepared by pulverizing and mixing the above amounts of active compound, carrier and emulsifier. A portion of the wettable powder containing the prescribed amount of the active compound is diluted with water to be subjected to the test mentioned below.

Testing Procedure

About 5 seeds of tomato (cultivar: Kurihara) were sown in each vinyl pot of a diameter of 7 cm, and raised in a greenhouse (at 15°–25° C.). The dilution obtained by diluting the prepared testing compound to the prescribed concentration as mentioned above, was sprayed at a rate of 25 ml per 3 pots over small seedlings reaching the 4 leaf stage. 10 days after the spraying, the zoosporangia formed on lesions, which had previously been infected and diseased with *Phytophthora infestans*, were washed down with a painting-brush into distilled water to prepare a suspension. The suspension was spray-inoculated on the treated plants and they were maintained in a greenhouse at 15°–20° C. 7 days after the inoculation, the infection degree per pot was evaluated and the control value was calculated. The results are average values of 3 pots. The phytotoxicity was concurrently examined. The results are shown in Table 3.

Use Example 4
Test of foliar spray against barley powdery mildew

Testing Procedure

About 10 seeds of barley (cultivar: Haruna 2jo) were sown in each vinyl pot of a diameter of 7 cm, and raised in a greenhouse (at 15°–25° C.). The dilution obtained by diluting the testing compound which had been prepared in the manner similar to that of Use Example 3, was sprayed at a rate of 25 ml per 3 pots over small seedlings reaching the 2 leaf stage. 5 days after the spraying, the conidiospores formed on lesions, which had previously been infected and diseased with *Erysiphe graminis*, were sprinkled over the treated barley leaves for inoculation, and the plants were maintained in a greenhouse at 15°–20° C. 7 days after the inoculation, the infection degree per pot was evaluated and the control value was calculated. The results are average values of 3 pots. The phytotoxicity was concurrently examined. The results are shown in Table 3.

TABLE 3

| Compound No. | Use Example 1 | Use Example 2 | Use Example 3 | Use Example 4 |
|---|---|---|---|---|
| 1 | ++ | ++ |  | ++++ |
| 2 | +++ | ++ |  |  |
| 3 | +++ | ++++ | ++++ | ++++ |
| 4 | ++ | + | + | + |
| 5 | + | +++ | + |  |
| 10 | ++++ | ++ | ++ | ++ |
| 13 | ++ | ++ | +++ | ++++ |
| 14 | +++ | ++++ | +++ | +++ |
| 18 | +++ | ++ | +++ | ++++ |
| 19 | +++ | + | ++ |  |
| 20 | ++ | + | ++ | ++++ |
| 24 | ++ | ++ | + |  |
| 25 | +++ | ++ | +++ | +++ |
| 26 | ++ | ++ |  | ++++ |

In the Table,
++++: control value, not less than 95%
+++: control value, not less than 85%
++: control value, not less than 70%
+: control value, not less than 50%

It will be understood that the specification and examples are illustrative but not limitative of the present invention and that other embodiments within the spirit and scope of the invention will suggest themselves to those skilled in the art.

We claim:

1. A chloropyridylcarbonyl derivative of the formula

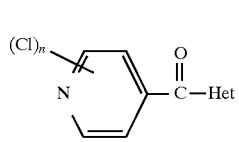

(I)

in which
Het is

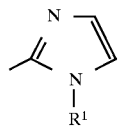

n is 1 and the chlorine atom is bonded to the 2-position of the pyridyl group or
n is 2 and the chlorine atoms are bonded to the 2- and 6-position of the pyridyl group,
$R^1$ is hydrogen or is $C_{1-4}$ alkyl, optionally substituted by one to three identical or different substituents selected from halogen, phenyl, cyano, $C_{1-4}$ alkoxy, $C_{1-4}$ alkoxycarbonyl, or R¹ is $C_{2-4}$ alkenyl, optionally substituted by one to three identical or different substituents selected from $C_{1-4}$ alkoxy or R¹ is phenyl.

2. A compound according to claim 1, wherein such compound is 2-(2',6'-dichloro-4'-pyridylcarbonyl)-imidazole of the formula

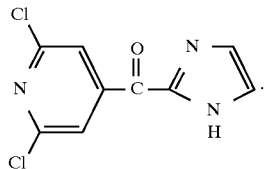

3. A compound according to claim 1, wherein such compound is 2-(2',6'-dichloro-4'-pyridylcarbonyl)-1-isopropyl-imidazole of the formula

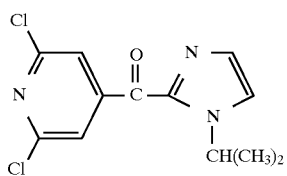

4. A microbicidal composition comprising a microbicidally effective amount of a compound according to claim 1 and an inert diluent.

5. A method of combating undesired microorganisms, which method comprises applying to such undesired microorganisms or to their habitat a microbicidally effective amount of a compound according to claim 1.

* * * * *